US008524931B2

(12) United States Patent
Xu et al.

(10) Patent No.: US 8,524,931 B2
(45) Date of Patent: Sep. 3, 2013

(54) PRECURSOR COMPOSITIONS FOR ALD/CVD OF GROUP II RUTHENATE THIN FILMS

(75) Inventors: Chongying Xu, New Milford, CT (US); Bryan C. Hendrix, Danbury, CT (US); Thomas M. Cameron, Newtown, CT (US); Jeffrey F. Roeder, Brookfield, CT (US); Matthias Stender, New Milford, CT (US); Tianniu Chen, Rocky Hill, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 847 days.

(21) Appl. No.: 12/523,704

(22) PCT Filed: Mar. 12, 2007

(86) PCT No.: PCT/US2007/063831
§ 371 (c)(1),
(2), (4) Date: Aug. 17, 2009

(87) PCT Pub. No.: WO2008/088563
PCT Pub. Date: Jul. 24, 2008

(65) Prior Publication Data
US 2010/0095865 A1 Apr. 22, 2010

Related U.S. Application Data

(60) Provisional application No. 60/885,404, filed on Jan. 17, 2007.

(51) Int. Cl.
*C07F 15/00* (2006.01)
*C03C 17/10* (2006.01)

(52) U.S. Cl.
USPC .......................................... 556/137; 106/1.24

(58) Field of Classification Search
USPC .................................. 556/136, 137; 106/1.24
See application file for complete search history.

(56) References Cited

U.S. PATENT DOCUMENTS

| | | |
|---|---|---|
| 4,927,670 A | 5/1990 | Erbil |
| 4,948,623 A | 8/1990 | Beach et al. |
| 5,453,494 A | 9/1995 | Kirlin et al. |
| 5,820,664 A | 10/1998 | Gardiner et al. |
| 5,840,897 A | 11/1998 | Kirlin et al. |
| 5,859,274 A | 1/1999 | Baum et al. |
| 5,916,359 A | 6/1999 | Baum et al. |
| 5,919,522 A | 7/1999 | Baum et al. |
| 6,002,036 A | 12/1999 | Kadokura |
| 6,018,065 A | 1/2000 | Baum et al. |
| 6,110,529 A | 8/2000 | Gardiner et al. |
| 6,111,122 A | 8/2000 | Paw et al. |
| 6,111,124 A | 8/2000 | Baum et al. |
| 6,117,571 A | 9/2000 | Baum et al. |
| 6,126,996 A | 10/2000 | Kirlin et al. |
| 6,214,105 B1 | 4/2001 | Hintermaier et al. |
| 6,218,518 B1 | 4/2001 | Baum et al. |
| 6,277,436 B1 | 8/2001 | Stauf et al. |
| 6,284,654 B1 | 9/2001 | Roeder et al. |
| 6,303,391 B1 | 10/2001 | Hintermaier et al. |
| 6,340,769 B1 | 1/2002 | Baum et al. |
| 6,342,445 B1 | 1/2002 | Marsh |
| 6,344,079 B1 | 2/2002 | Baum |
| 6,444,264 B2 | 9/2002 | Hintermaier et al. |
| 6,599,447 B2 | 7/2003 | Stauf et al. |
| 6,869,638 B2 | 3/2005 | Baum et al. |
| 6,884,901 B2 | 4/2005 | Thompson et al. |
| 6,921,062 B2 | 7/2005 | Gregg et al. |
| 6,984,591 B1 | 1/2006 | Buchanan et al. |
| 7,005,392 B2 | 2/2006 | Baum et al. |
| 7,211,509 B1 | 5/2007 | Gopinath et al. |
| 7,226,640 B2 | 6/2007 | Baum et al. |
| 7,285,308 B2 | 10/2007 | Hendrix et al. |
| 7,300,038 B2 | 11/2007 | Gregg et al. |
| 7,323,581 B1 | 1/2008 | Gardiner et al. |
| 7,531,679 B2 | 5/2009 | Wang et al. |
| 7,635,441 B2 | 12/2009 | Kadokura et al. |
| 2002/0192899 A1 | 12/2002 | Shimamoto et al. |
| 2003/0020122 A1 | 1/2003 | Joo et al. |
| 2004/0166671 A1 | 8/2004 | Lee et al. |
| 2004/0215030 A1 | 10/2004 | Norman |

(Continued)

FOREIGN PATENT DOCUMENTS

JP 2006-037123 A 2/2006
KR 10-2008-0079514 A 9/2008

(Continued)

OTHER PUBLICATIONS

Smith et al., Angew. Chem., vol. 105, No. 9, p. 1355 (1993).*
Koelle et al., Organometallics, vol. 16, No. 15, pp. 3273-3281 (1997).*
Terasawa et al., Organometallics, vol. 24, No. 11, pp. 2713-2721 (2005).*
Anderson, Q. et al., "Synthesis and Characterization of the First Pentaphenylcyclopentadienyl Copper Complex (Ph5CP)Cu(PPh3)", "Organometallics", 1998, pp. 4917-4920, vol. 17.
Artaud-Gillet, M.C. et al., "Evaluation of copper organometallic sources for CuGaSe2 photovoltaic applications", "Journal of Crystal Growth", 2003, pp. 163-168, vol. 248.

(Continued)

*Primary Examiner* — Porfirio Nazario Gonzalez
(74) *Attorney, Agent, or Firm* — Hultquist, PLLC; Mary B. Grant; Maggie Chappuis

(57) ABSTRACT

Precursor compositions useful for atomic layer deposition (ALD) and chemical vapor deposition (CVD) of strontium ruthenium oxide ($SrRuO_3$) thin films, e.g., in the manufacture of microelectronic devices, as well as processes of making and using such precursors, and precursor supply systems containing such precursor compositions in packaged form. Cyclopentadienyl compounds of varied type are described, including cyclopentadienyl as well as non cyclopentadienyl ligands coordinated to ruthenium, strontium or barium central atoms. The precursors of the invention are useful for forming contacts for microelectronic memory device structures, and in a specific aspect for selectively coating copper metallization without deposition on associated dielectric, under deposition conditions in a forming gas ambient.

4 Claims, 2 Drawing Sheets

(56) References Cited

U.S. PATENT DOCUMENTS

| | | |
|---|---|---|
| 2005/0153073 A1 | 7/2005 | Zheng et al. |
| 2006/0035462 A1 | 2/2006 | Millward |
| 2006/0128150 A1 | 6/2006 | Gandikota et al. |
| 2006/0141155 A1 | 6/2006 | Gordon et al. |
| 2006/0292841 A1 | 12/2006 | Quick |
| 2007/0054487 A1 | 3/2007 | Ma et al. |
| 2007/0134417 A1 | 6/2007 | Baum et al. |
| 2008/0254218 A1 | 10/2008 | Lei et al. |
| 2009/0002917 A1 | 1/2009 | Kil et al. |
| 2009/0084288 A1 | 4/2009 | Wang et al. |
| 2009/0112009 A1 | 4/2009 | Chen et al. |
| 2009/0208637 A1 | 8/2009 | Chen et al. |

FOREIGN PATENT DOCUMENTS

| | | |
|---|---|---|
| SU | 768457 A | 10/1980 |
| WO | 0015865 A1 | 3/2000 |
| WO | 2004046417 A2 | 6/2004 |
| WO | 2006012052 A2 | 2/2006 |
| WO | 2007064376 A2 | 6/2007 |
| WO | 2008057616 A2 | 5/2008 |
| WO | 2008128141 A2 | 10/2008 |
| WO | 2009020888 A1 | 2/2009 |
| WO | 2009059237 A2 | 5/2009 |

OTHER PUBLICATIONS

Macomber, D. et al , "n5—Cyclopentadienyl- and n5-Pentamethylcyclopentadienyl copper compunds Containng Phosphine, Carbonyl, and n2 -Acetyle", "J. Am. Chem.", 1983, pp. 5325-5329, vol. 105.

Ren, H. et al. , "Sythesis and structures of cyclopentadienyl N-heterocyclic carbene copper complexes", "Journal of Organometallic Chemistry", 2006, pp. 4109-4113, vol. 691.

Papadatos, Filippos, et al., "Characterization of Ruthenium and Ruthenium Oxide Thin Films deposited by Chemical Vapor Deposition for CMOS Gate . . .", "Mat. Res. Soc. Symp. Proc.", 2003, pp. N3.3.1-N3.3.6, vol. 745.

U.S. Appl. No. 12/507,048.

U.S. Appl. No. 12/523,704.

U.S. Appl. No. 12/507,901.

Karsch, H. et al "Bis(amidinate) Complexes of Silicon and Germanium", "Eur. J. Inorg. Chemistry", 1998, pp. 433-436.

* cited by examiner

PRECURSOR COMPOSITIONS FOR ALD/CVD OF GROUP II RUTHENATE THIN FILMS

CROSS-REFERENCE TO RELATED APPLICATIONS

This application is a U.S. national phase under the provisions of 35 USC §371 of International Application No. PCT/US07/63831 filed Mar. 12, 2007, which in turn claims priority of U.S. Provisional Patent Application No. 60/885,404 filed Jan. 17, 2007. The disclosures of such international application and U.S. priority application are hereby incorporated herein by reference in their respective entireties, for all purposes.

FIELD OF THE INVENTION

The present invention relates to Group II ruthenate precursor compositions useful for atomic layer deposition (ALD) and chemical vapor deposition (CVD) of ruthenium and ruthenium-containing thin films, e.g., strontium ruthenium oxide ($SrRuO_3$) thin films. Such Group II ruthenates are useful in the manufacture of microelectronic devices. The invention also relates to processes of making and using such precursors, to products formed using such precursor compositions, and to precursor supply systems comprising such precursor compositions in packaged form.

DESCRIPTION OF THE RELATED ART

Among the Group II ruthenates, strontium ruthenium oxide ($SrRuO_3$, or SRO) thin films are potentially attractive as conductive electrode materials for memory applications. Related materials that are candidates for construction of electrodes include other Group II ruthenates, e.g., such as $CaRuO_3$ (CRO).

Uniform conformal coating involving greater than 90% step coverage on high aspect ratio structures is required for such ruthenates in memory device applications, e.g., in non-volatile ferroelectronic memories and DRAMs.

Atomic layer deposition (ALD) is currently being explored as a technique for achieving such coverage. It is difficult, however, to achieve satisfactory uniform coating of strontium ruthenium oxide thin films using the precursors that have been developed to date. Similar deficiencies are encountered when chemical vapor deposition (CVD) is used as a deposition technique to form such ruthenate films.

In addition to the foregoing problem of lack of conformality of the thin-film deposited on the substrate, deposition of conformal Ru materials using ALD/CVD techniques requires monomeric metal precursors that are transportable (volatile) at temperatures specific to the specific ALD/CVD process. It also has been difficult when using prior art precursors to achieve uniform distribution of ruthenium within the deposited ruthenate film.

Additional difficulties involving use of ruthenium precursors relate to process condition requirements. Ruthenium may deposit efficiently on a certain surfaces but not others depending on the gas environment of the deposition process, and in some gas environments, ruthenium deposition rate is negligible on all surfaces. The ambient gas environment of the deposition operation therefore has a highly significant role in determining the viability of a specific precursor for effective use.

In consequence, the art continues to seek new precursors and process conditions for deposition of Group II ruthenate thin films, e.g., films of strontium ruthenium oxide, calcium ruthenium oxide and barium ruthenium oxide.

SUMMARY OF THE INVENTION

The present invention relates to precursor compositions useful for atomic layer deposition (ALD) and chemical vapor deposition (CVD) of Group II ruthenates, such as strontium ruthenium oxide ($SrRuO_3$, or SRO), calcium ruthenium oxide (CRO) and barium ruthenium oxide (BRO) thin films. The invention also contemplates methods of making and using such precursors, and microelectronic devices including Group II ruthenate films as deposited from such precursors, and packages containing such precursor compositions for supply to a deposition installation.

In one aspect, the invention relates to a ruthenium precursor useful for atomic layer deposition and/or chemical vapor deposition, comprising a ruthenium central atom to which is coordinated at least one cyclopentadienyl ligand, wherein the cyclopentadienyl moiety has the formula

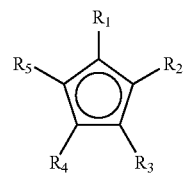

wherein each of $R_1$, $R_2$, $R_3$, $R_4$ and $R_5$ can be the same as or different from the others, and each is independently selected from among hydrogen, $C_1$-$C_{12}$ alkyl, $C_1$-$C_{12}$ alkylamino (including monoalkylamino as well as dialkylamino substitutent species in such term), $C_3$-$C_8$ cycloalkyl, $C_6$-$C_{12}$ aryl, $C_5$-$C_{12}$ heteroaryl, $C_1$-$C_{12}$ alkoxy, $C_3$-$C_6$ alkylsilyl, $C_2$-$C_{12}$ alkenyl, $R^1R^2NNR^3$, wherein $R^1$, $R^2$ and $R^3$ may be the same as or different from one another and each is independently selected from hydrogen and $C_1$-$C_6$ alkyl, and pendant ligands including functional group(s) providing further coordination to the ruthenium central atom, and selected from among aminoalkyl, alkoxyalkyl, aryloxyalkyl, imidoalkyl, and acetylalkyl, having the following formulae:

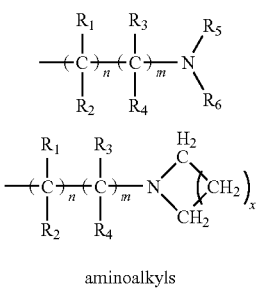

aminoalkyls wherein: the methylene (—$CH_2$—) moiety could alternatively be another divalent hydrocarbyl moiety; each of $R_1$-$R_4$ is the same as or different from one another, with each being independently selected from among hydrogen, $C_1$-$C_6$ alkyl and $C_6$-$C_{10}$ aryl; each of $R_5$ and $R_6$ is the same as or different from the other, with each being independently selected from among hydrogen, $C_1$-$C_6$ alkyl; n and m are each selected independently as having a value of from 0 to 4, with the proviso that m and n cannot be 0 at the same time, and x is selected from 1 to 5;

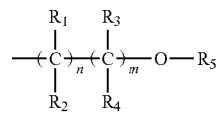

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among hydrogen, $C_1$-$C_6$ alkyl, and $C_6$-$C_{10}$ aryl; and n and m are selected independently as having a value of from 0 to 4, with the proviso that m and n cannot be 0 at the same time;

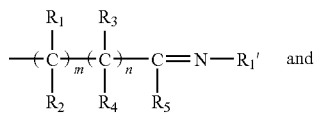

imidoalkyl wherein each of $R_1$, $R_2$, $R_3$, $R_4$, $R_5$ is the same as or different from one another, with each being independently selected from among hydrogen, $C_1$-$C_6$ alkyl, and $C_6$-$C_{10}$ aryl; each of $R_1'$, $R_2'$ is the same as or different from one another, with each being independently selected from hydrogen, $C_1$-$C_6$ alkyl, and $C_6$-$C_{10}$ aryl; and n and m are selected independently from 0 to 4, with the proviso that m and n cannot be 0 at the same time;

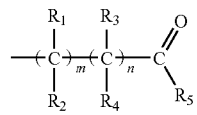

acetylalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among hydrogen, hydroxyl, acetoxy, $C_1$-$C_6$ alkyl, $C_1$-$C_{12}$ alkylamino, $C_6$-$C_{10}$ aryl, and $C_1$-$C_5$ alkoxy; and n and m are selected independently from 0 to 4, with the proviso that m and n cannot be 0 at the same time.

Another aspect of the invention relates to a ruthenium compound containing at least one cyclopentadienyl ligand, and at least one further ligand selected from among amidinate, guanidinate, beta-diketonate, beta-diketoiminate, isoureate, and beta-diketiminate ligands.

In a further aspect, the invention relates to a mixed ligand monomeric Cp complex of ruthenium (II) in which the non-Cp ligand is selected from among amidinate, guanidinate, beta-diketiminate, and related nitrogen-based ligands.

Yet another aspect of the invention relates to a method of making a mixed ligand monomeric Cp complex of ruthenium (II) according to the invention, such method comprising reacting a cyclopentadienyl ruthenium halide or alkoxide with a lithium salt of a corresponding amidinates, guanidinates, beta-diketiminates, or related nitrogen-based ligand.

The invention in another aspect relates to a mixed ligand monomeric Cp complex of ruthenium, strontium, calcium or barium, selected from among:

(A) ruthenium compounds selected from among the following compounds (1)-(5):

(1) ruthenium beta-diketiminate compounds of the formula

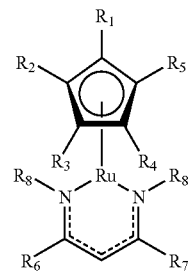

wherein each of $R_1$, $R_2$, $R_3$, $R_4$ and $R_5$ is as described in paragraph [0009] hereof, and each of $R_6$, $R_7$, and $R_8$ can be the same as or different from the others, and is independently selected from hydrogen, $C_1$-$C_6$ alkyl, $C_6$-$C_{10}$ aryl, $C_1$-$C_6$ alkylamine, silyl, and substituted silyl wherein the silyl substituents can be any suitable organo substituents, e.g., $C_1$-$C_6$ alkyl, such as trimethylsilyl;

(2) ruthenium beta-diketoiminate compounds of the formula

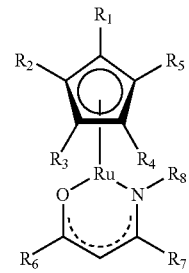

wherein each of $R_1$, $R_2$, $R_3$, $R_4$, and $R_5$ is as described in paragraph [0009] hereof, and each of $R_6$, $R_7$, and $R_8$ can be the same as or different from the others, and is independently selected from hydrogen, $C_1$-$C_6$ alkyl, $C_6$-$C_{10}$ aryl, $C_1$-$C_6$ alkylamine, silyl, and substituted silyl wherein the silyl substituents can be any suitable organo substituents, e.g., $C_1$-$C_6$ alkyl, such as trimethylsilyl;

(3) ruthenium acetylacetonate compounds of the formula

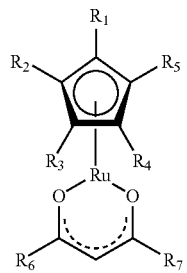

wherein each of $R_1$, $R_2$, $R_3$, $R_4$ and $R_5$ is as described in paragraph [0009] hereof, and each of $R_6$, and $R_7$ can be the same as or different from the other, and is independently selected from hydrogen, $C_1$-$C_6$ alkyl, $C_6$-$C_{10}$ aryl, $C_1$-$C_6$ alkylamine, silyl, and substituted silyl wherein the silyl substituents can be any suitable organo substituents, e.g., $C_1$-$C_6$ alkyl, such as trimethylsilyl;

(4) ruthenium amidinate compounds of the formula:

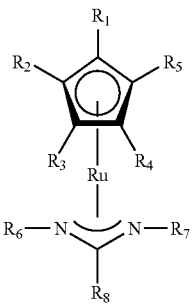

wherein each of $R_1$, $R_2$, $R_3$, $R_4$ and $R_5$ is as described in paragraph [0009] hereof, and each of $R_6$, $R_7$, and $R_8$ can be the same as or different from the others, and is independently selected from hydrogen, $C_1$-$C_5$ alkyl, $C_6$-$C_{10}$ aryl, $C_3$-$C_9$ cycloalkyl, silyl, and substituted silyl wherein the silyl substituents can be any suitable organo substituents, e.g., $C_1$-$C_6$ alkyl, such as trimethylsilyl;

(5) ruthenium guanidinate compounds of the formula:

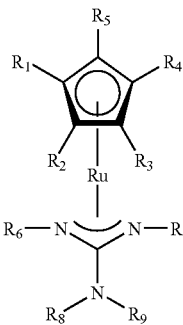

wherein each of $R_1$, $R_2$, $R_3$, $R_4$ and $R_5$ is as described in paragraph [0009] hereof, and each of $R_6$, $R_7$, $R_8$ and $R_9$ can be the same as or different from the others, and is independently selected from hydrogen, $C_1$-$C_5$ alkyl, $C_6$-$C_{10}$ aryl, $C_3$-$C_9$ cycloalkyl silyl, and substituted silyl wherein the silyl substituents can be any suitable organo substituents, e.g., $C_1$-$C_6$ alkyl, such as trimethylsilyl;

6) ruthenium isoureate compounds of the formula

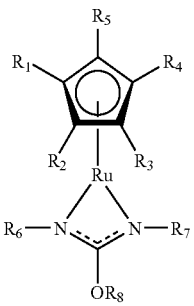

wherein each of $R_1$, $R_2$, $R_3$, $R_4$ and $R_5$ is as described in paragraph [0009] hereof, and each of $R_6$, $R_7$ and $R_8$ can be the same as or different from the others, and is independently selected from hydrogen, $C_1$-$C_5$ alkyl, $C_6$-$C_{10}$ aryl, $C_3$-$C_9$ cycloalkyl, silyl, and substituted silyl wherein the silyl substituents can be any suitable organo substituents, e.g., $C_1$-$C_6$ alkyl, such as trimethylsilyl;

(B) strontium compounds selected from among compounds having the same formulae as ruthenium compounds (A) (1)-(6), having strontium as a central atom in place of ruthenium;

(C) calcium compounds selected from among compounds having the same formulae as ruthenium compounds (A) (1)-(6), having calcium as a central atom in place of ruthenium; and (D) barium compounds selected from among compounds having the same formulae as ruthenium compounds (A) (1)-(6), having barium as a central atom in place of ruthenium.

Another aspect of the invention relates to a method of making a ruthenium beta-diketiminate, comprising a salt elimination reaction conducted according to the following reaction scheme, wherein Cp* denotes the pentamethylcyclopentadienyl ligand, $C_5Me_5$:

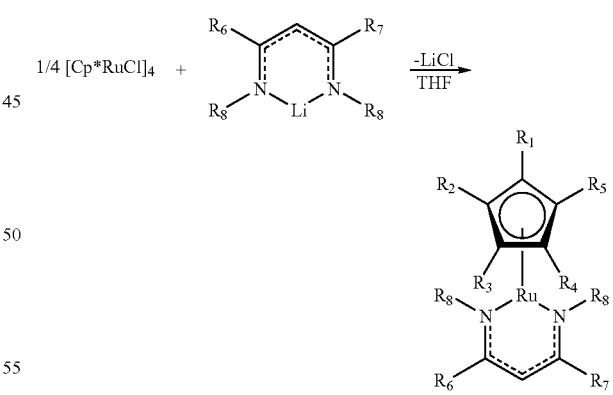

wherein each of $R_1$, $R_2$, $R_3$, $R_4$, $R_5$, $R_6$, $R_7$, and $R_8$ can be the same as or different from the others, and is independently selected from hydrogen, $C_1$-$C_6$ alkyl, $C_6$-$C_{10}$ aryl, $C_1$-$C_6$ alkylamine, silyl, and substituted silyl wherein the silyl substituents can be any suitable organo substituents, e.g., $C_1$-$C_6$ alkyl, such as trimethylsilyl.

A further aspect of the invention relates to a method of making a ruthenium beta-diketiminate, comprising an amine elimination reaction conducted according to the following reaction scheme:

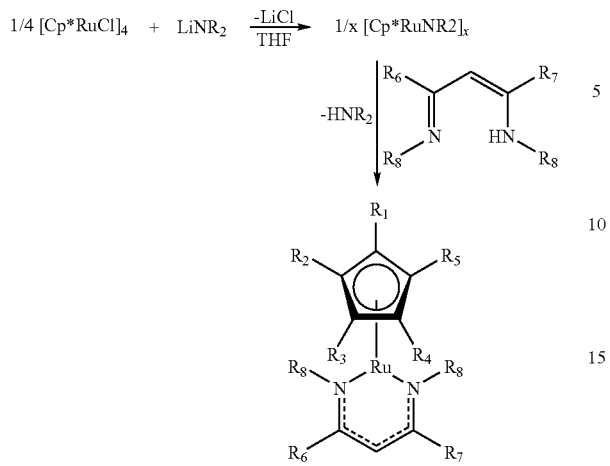

wherein each of $R_1$, $R_2$, $R_3$, $R_4$, $R_5$, $R_6$, $R_7$, and $R_8$ can be the same as or different from the others, and is independently selected from hydrogen, $C_1$-$C_6$ alkyl, $C_6$-$C_{10}$ aryl, $C_1$-$C_6$ alkylamine, silyl, and substituted silyl wherein the silyl substituents can be any suitable organo substituents, e.g., $C_1$-$C_6$ alkyl, such as trimethylsilyl.

Still another aspect of the invention relates to a method of making a ruthenium-diketoiminate (corresponding barium-, strontium- and calcium-diketoiminates can be formed in similar manner), comprising a reaction conducted according to the following reaction scheme:

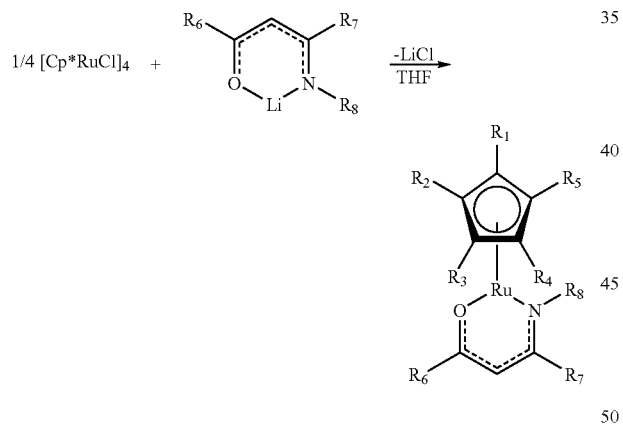

wherein each of $R_1$, $R_2$, $R_3$, $R_4$, $R_5$, $R_6$, $R_7$, and $R_8$ can be the same as or different from the others, and is independently selected from hydrogen, $C_1$-$C_6$ alkyl, $C_6$-$C_{10}$ aryl, $C_1$-$C_6$ alkylamine, silyl, and substituted silyl wherein the silyl substituents can be any suitable organo substituents, e.g., $C_1$-$C_6$ alkyl, such as trimethylsilyl.

In another aspect, the invention relates to a method of making a ruthenium-acetylacetonate, comprising a reaction conducted according to the following reaction scheme:

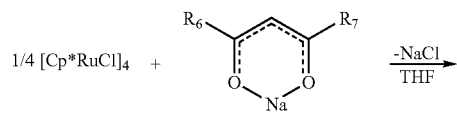

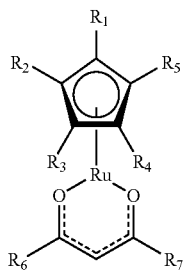

wherein each of $R_1$, $R_2$, $R_3$, $R_4$, $R_5$, $R_6$, and $R_7$ can be the same as or different from the others, and is independently selected from hydrogen, $C_1$-$C_6$ alkyl, $C_6$-$C_{10}$ aryl, $C_1$-$C_6$ alkylamine, silyl and substituted silyl wherein the silyl substituents can be any suitable organo substituents, e.g., $C_1$-$C_6$ alkyl, such as trimethylsilyl.

Another aspect of the invention relates to a precursor composition useful in conformal ALD or CVD deposition of ruthenium-containing films, e.g., a strontium ruthenium oxide film, in which the precursor composition includes at least one compound selected from among:

A) $Ru(Cp)_2$ and $Sr(Cp)_2$, wherein Cp is cyclopentadienyl of the formula

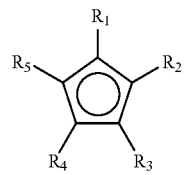

wherein each of $R_1$, $R_2$, $R_3$, $R_4$ and $R_5$ can be the same as or different from the others, and each is independently selected from among hydrogen, $C_1$ to $C_6$ alkyl, $C_3$-$C_8$ cycloalkyl, $C_6$-$C_{12}$ aryl, $C_1$ to $C_6$ alkoxy, silyl, $C_1$ to $C_6$ alkylsilyl, and pendant ligands with additional functional group(s) that provides further coordination to the metal center;

B) $Ru(beta\text{-}diketonate)_x\text{-}L_y$ and $Sr(beta\text{-}diketonate)_2\text{-}L_z$ wherein the beta-diketonate moiety has the formula

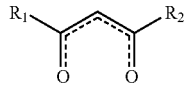

wherein:

x has a value of 2 or 3, y is an integer having a value of from 0 to 2, and z is an integer having a value of from 0 to 4;

$R_1$ and $R_2$ can be the same as or different from one another, and each is independently selected from among $C_1$ to $C_6$ alkyl, $C_6$ to $C_{10}$ aryl, $C_1$ to $C_6$ alkoxy, $C_1$ to $C_6$ alkylsilyl, and pendant ligands with additional functional group(s) that provides further coordination to the metal center; and L is selected from among neutral Lewis bases, such as alkenes, alkynes, amines, polyamines, polyethers, and preferably from among tertiary phosphines, azoles, imidazoles, pyridines, and bipyridines;

C) Ru(beta-diketoiminate)$_x$-L$_y$, and Sr(beta-diketoiminate)$_2$-L$_z$ wherein beta-diketoiminate has the formula

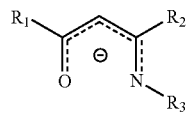

wherein:

x has a value of 2 or 3, y is an integer having a value of from 0 to 2, and z is an integer having a value of from 0 to 4;

each of $R_1$, $R_2$ and $R_3$ can be the same as or different from one another, and each is independently selected from among $C_1$ to $C_6$ alkyl, $C_6$ to $C_{10}$ aryl, $C_1$ to $C_6$ alkoxy, $C_1$ to $C_6$ alkylsilyl, and pendant ligands with additional functional group(s) that provide further coordination to the metal center; and L is selected from among neutral Lewis bases such as alkenes, alkynes, polyamines, polyethers, etc.; and D) Ru(beta-diketiminate)$_x$-L$_y$, and Sr(beta-diketiminate)$_2$-L$_z$, wherein beta-diketiminate has the formula

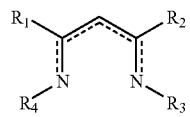

wherein:

x has a value of 2 or 3, y is an integer having a value of from 0 to 2, and z is an integer having a value of from 0 to 4;

each of $R_1$, $R_2$, $R_3$ and $R_4$ can be the same as or different from one another, and each is independently selected from among $C_1$ to $C_6$ alkyl, $C_6$ to $C_{10}$ aryl, $C_1$ to $C_6$ alkoxy, $C_1$ to $C_6$ alkylsilyl, and pendant ligands with additional functional group(s) that provide further coordination to the metal center; and L is selected from among neutral Lewis bases, such as, alkenes, alkynes, polyamines, polyethers, etc.

In the cyclopentadienyl rings in compounds of the present invention, the substituents on the ring carbon atoms can include any suitable substituent species, each of which may be the same as or different from the others, with each being independently selected from among hydrogen, $C_1$-$C_{12}$ alkyl, $C_1$-$C_{12}$ alkylamino, $C_6$-$C_{10}$ aryl, $C_1$-$C_{12}$ alkoxy, $C_3$-$C_6$ alkylsilyl, $C_2$-$C_{12}$ alkenyl, $R^1R^2NNR^3$, wherein $R^1$, $R^2$ and $R^3$ may be the same as or different from one another and each is independently selected from $C_1$-$C_6$ alkyl, and pendant ligands including functional group(s) providing further coordination to the central atom, and selected from among aminoalkyl, alkoxyalkyl, aryloxyalkyl, imidoalkyl, and acetylalkyl, having the following formulae:

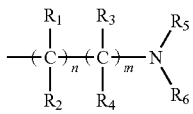

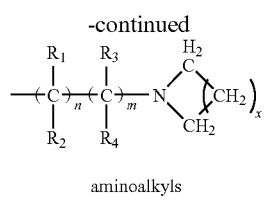

aminoalkyls wherein: the methylene (—CH$_2$—) moiety could alternatively be another divalent hydrocarbyl moiety; each of $R_1$-$R_4$ is the same as or different from one another, with each being independently selected from among hydrogen, $C_1$-$C_6$ alkyl and $C_6$-$C_{10}$ aryl; each of $R_5$ and $R_6$ is the same as or different from the other, with each being independently selected from among $C_1$-$C_6$ alkyl; n and m are each selected independently as having a value of from 0 to 4, with the proviso that m and n cannot be 0 at the same time, and x is selected from 1 to 5;

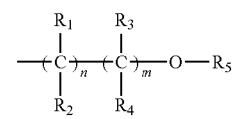

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently as having a value of from 0 to 4, with the proviso that m and n cannot be 0 at the same time;

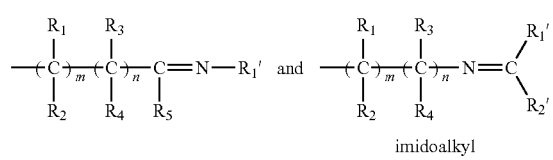

imidoalkyl wherein each of $R_1$, $R_2$, $R_3$, $R_4$, $R_5$ is the same as or different from one another, with each being independently selected from among hydrogen, $C_1$-$C_6$ alkyl, and $C_6$-$C_{10}$ aryl; each of $R_1'$, $R_2'$ is the same as or different from one another, with each being independently selected from $C_1$-$C_6$ alkyl, and $C_6$-$C_{10}$ aryl; and n and m are selected independently from 0 to 4, with the proviso that m and n cannot be 0 at the same time;

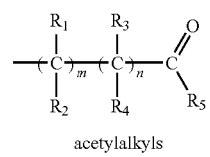

acetylalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, $C_6$-$C_{10}$ aryl, and $C_1$-$C_5$ alkoxy; and n and m are selected independently from 0 to 4, with the proviso that m and n cannot be 0 at the same time.

In another aspect, the invention relates to a solid delivery process for atomic layer deposition or chemical vapor deposition of a metal film a substrate, comprising volatilizing a solid precursor composition of the present invention to form a precursor vapor, and contacting said precursor vapor with the substrate to deposit said metal film thereon, wherein said precursor composition comprises a mixed ligand cyclopentadienyl metal compound including a cyclopentadienyl ligand and at least one non-cyclopentadienyl ligand, wherein the metal is selected from the group consisting of ruthenium, strontium, calcium, and barium.

A further aspect of the invention relates to a solid delivery process for atomic layer deposition or chemical vapor deposition of a metal film on a substrate, comprising volatilizing a solid precursor composition of the present invention to form a precursor vapor, and contacting said precursor vapor with the substrate to deposit said metal film thereon, wherein said precursor composition comprises a dicyclopentadienyl metal compound, wherein the metal is selected from the group consisting of ruthenium, strontium, calcium, and barium.

In a still further aspect, the invention relates to a method of fabricating a microelectronic device including metallization material and dielectric material in proximity to said metallization material, comprising depositing ruthenium on said metallization material from a precursor vapor of a ruthenium precursor under deposition conditions including a forming gas ambient vapor environment, wherein the ruthenium precursor comprises a cyclopentadienyl ruthenium precursor that under said deposition conditions deposits ruthenium from said precursor vapor on the metallization material but does not deposit ruthenium on said dielectric material.

The invention relates in another aspect to a precursor dispensing package, comprising a precursor storage and dispensing vessel, and a ruthenium, strontium, calcium, or barium precursor of the invention contained in such precursor storage and dispensing vessel.

A further aspect of the invention relates to a selective deposition process for forming a ruthenium-containing film on a substrate including metal and non-metal portions, such process comprising depositing the ruthenium-containing film on the substrate from a precursor vapor of a ruthenium precursor in an ambient gas environment limiting the deposition of the ruthenium-containing film on the non-metal portions of the substrate from the precursor.

In yet another aspect, the invention relates to a ruthenium selective deposition process, comprising conducting ruthenium deposition in a gaseous environment that is effective to enhance selectivity of ruthenium deposition on a surface of interest on a substrate, as compared to corresponding selectivity in an inert gas environment.

Another aspect of the invention relates to a method of depositing a Group II metal ruthenate film on a substrate by a vapor deposition process, such method comprising conducting the vapor deposition process with precursors including a ruthenium precursor and a Group II metal precursor including strontium, calcium or barium, wherein the ruthenium precursor and the Group II metal precursor have at least one common ligand in relation to each other.

The invention in a further aspect relates to a method of depositing a Group II metal ruthenate film a substrate by an ALD or digital CVD vapor deposition process, such method comprising conducting the vapor deposition process with precursors including a ruthenium precursor and a Group II precursor including strontium, calcium or barium, wherein the ruthenium precursor and the Group II metal precursor lack any common ligand, and conducting a purge pulse between ruthenium precursor contacting of the substrate and Group II metal precursor contacting of the substrate.

As used herein, the identification of a carbon number range, e.g., in $C_1$-$C_{12}$ alkyl or $C_6$-$C_{12}$ aryl, is intended to include each of the component carbon number moieties within such range. Accordingly, $C_1$-$C_{12}$ alkyl is intended to include methyl, ethyl, propyl, butyl, pentyl and hexyl, including a straight chain as well as branched groups of such types. It therefore is to be appreciated that identification of a carbon number range, e.g., $C_1$-$C_6$, as broadly applicable to a substituent moiety, enables, in specific embodiments of the invention, the carbon number range to be further restricted, as a subgroup of moieties having a carbon number range within the broader specification of the substituent moiety. By way of example, the carbon number range e.g., $C_1$-$C_6$ alkyl, maybe more restrictively specified, in particular embodiments of the invention, to encompass sub-ranges such as $C_1$-$C_4$ alkyl, $C_2$-$C_6$ alkyl, $C_2$-$C_4$ alkyl, $C_3$-$C_5$ alkyl, or any other sub-range within the broad carbon number range.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
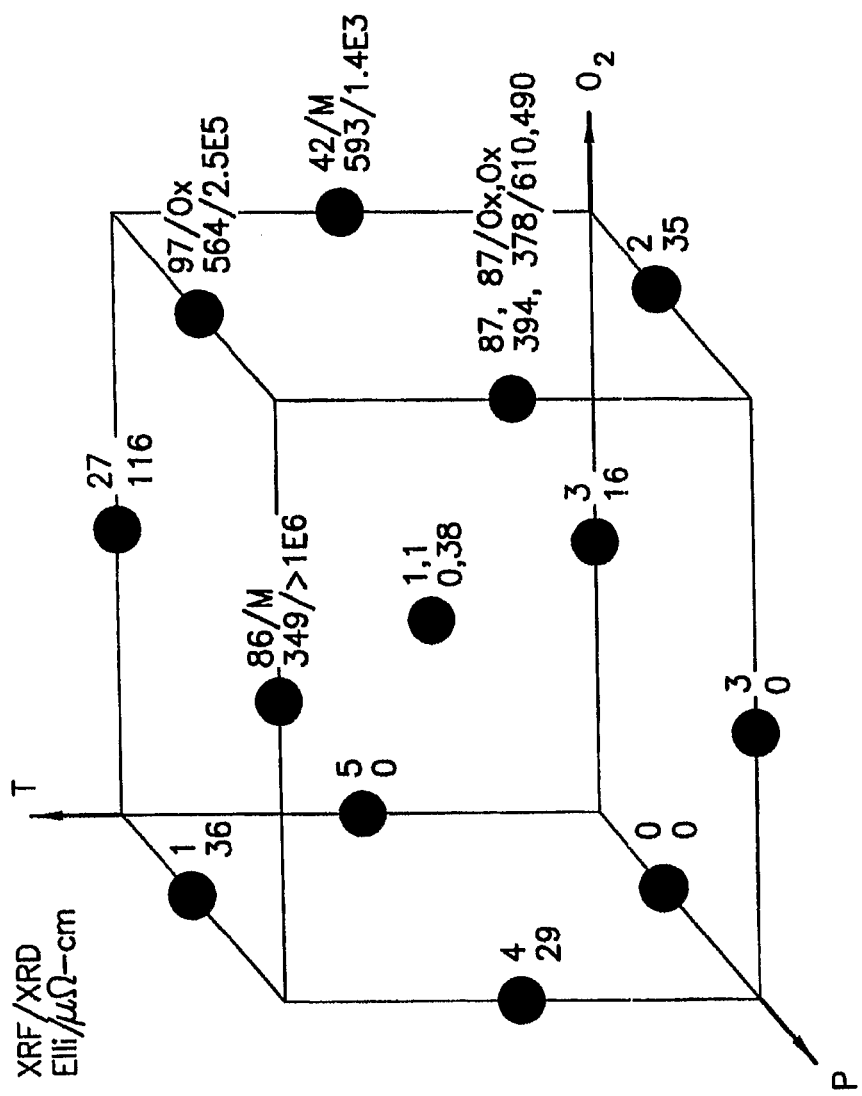
FIG. 1 is a shows the deposition of Ru determined by x-ray diffraction (XRD) and x-ray fluorescence (XRF) techniques, in which the respective axes represent oxygen concentration ($O_2$), process pressure (P in Torr), and temperature (T in ° C.), for a silicon oxide surface having a ruthenium film thereon, in a CVD aspect of the invention utilizing $Ru(EtCp)_2$ as the Ru precursor.

The present invention relates to precursor compositions useful for atomic layer deposition (ALD) and chemical vapor deposition (CVD) of Group II ruthenates, e.g., strontium ruthenium oxide ($SrRuO_3$, or SRO) thin films, calcium ruthenium oxide films, and barium ruthenium oxide films. The invention also relates to methods of making and using such precursors, to microelectronic devices including corresponding deposited metal films, and to packages containing such precursor compositions. The CVD process can be of any suitable type, including, for example, low-pressure CVD applications, assisted CVD processes, digital CVD processes (i.e., rapid vapor deposition, RVD), etc.

The invention as described hereinafter includes various ruthenium, calcium, barium, and strontium precursors containing cyclopentadienyl moieties coordinated to the metal central atom. The cyclopentadienyl rings in such cyclopentadienyl moieties

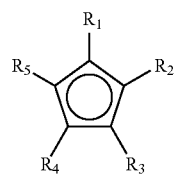

may be variously substituted, by substituents $R_1$, $R_2$, $R_3$, $R_4$ and $R_5$ that are independently selected from among hydrogen, $C_1$-$C_{12}$ alkyl, $C_1$-$C_{12}$ alkylamino, $C_3$-$C_8$ cycloalkyl, $C_6$-$C_{12}$ aryl, $C_5$-$C_{12}$ heteroaryl (i.e., aryl including heteroatoms, such as N, S, O, etc., in the aryl ring, e.g., pyridinyl), $C_1$-$C_{12}$ alkoxy, $C_3$-$C_6$ alkylsilyl, $C_2$-$C_{12}$ alkenyl (such term being intended to be broadly construed to include substituents containing linear, branched, and/or cyclic moieties containing ethylenic unsaturation, e.g., vinyl, allyl, cyclic-ene species, etc., and substituents containing various types of such moieties therein, e.g., tetramethylpentadienylvinyl), $R^1R^2NNR^3$, wherein $R^1$, $R^2$ and $R^3$ may be the same as or different from one another and each is independently selected from hydrogen and $C_1$-$C_6$ alkyl, and pendant ligands including functional group(s) providing further coordination to the metal center, such as, for example, alkoxyalkyl, aryloxyalkyl, imidoalkyl, and acetylalkyl, wherein suitable groups in these classes include those of the following formulae:

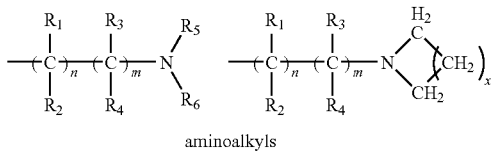

aminoalkyls wherein: the methylene (—$CH_2$—) moiety could alternatively be another divalent hydrocarbyl moiety; each of $R_1$-$R_4$ is the same as or different from one another, with each being independently selected from among hydrogen, $C_1$-$C_6$ alkyl and $C_6$-$C_{10}$ aryl; each of $R_5$ and $R_6$ is the same as or different from the other, with each being independently selected from among $C_1$-$C_6$ alkyl; n and m are each selected independently as having a value of from 0 to 4, with the proviso that m and n cannot be 0 at the same time, and x is selected as having a value of from 1 to 5;

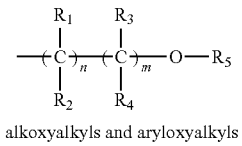

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl and $C_6$-$C_{10}$ aryl; and n and m are selected independently from 0 to 4, with the proviso that m and n cannot be 0 at the same time;

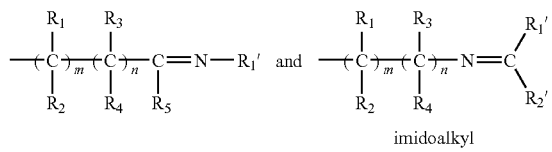

imidoalkyl wherein each of $R_1$, $R_2$, $R_3$, $R_4$ and $R_5$ is the same as or different from one another, with each being independently selected from among hydrogen, $C_1$-$C_6$ alkyl, and $C_6$-$C_{10}$ aryl; each of $R_1'$, $R_2'$ is the same as or different from one another, with each being independently selected from among $C_1$-$C_6$ alkyl, and $C_6$-$C_{10}$ aryl; and n and m are selected independently as having a value of from 0 to 4, with the proviso that m and n cannot be 0 at the same time;

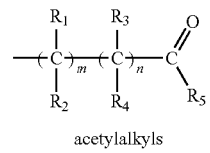

acetylalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, $C_6$-$C_{10}$ aryl, and $C_1$-$C_5$ alkoxy; and n and m are selected independently as having value of from 0 to 4, with the proviso that m and n cannot be 0 at the same time.

The invention in one specific aspect relates to monomeric cyclopentadienyl ruthenium compounds with co-ligands, as useful for deposition applications.

Such co-ligands may for example include amidinate, guanidinate and/or beta-diketiminate ligands. The co-ligands may in specific embodiments of the invention be constituted to include amidinate, guanidinate, isoureate, beta-diketonate, beta-diketoiminate and/or beta-diketiminate ligands. In other embodiments of the invention, the co-ligands may be constituted to exclude as a substituent species any of the various co-ligands specifically discussed hereinafter, in constituting a selection group of co-ligand species from which the co-ligands are selected in a given application of the ruthenium precursors of the present invention.

The use of amidinate, guanidinate, beta-diketiminates and related ligands in addition to the cyclopentadienyl (Cp) ligand provides sterically advantageous conformations of monomeric ruthenium precursors suitable for deposition processes. Such precursors enable highly uniform ruthenium distribution to be achieved in product films. In some applications of the invention, the precursor may comprise a cyclopentadienyl ruthenium complex that is dimeric in the solid state but in equilibrium with corresponding monomer in solution.

The invention thus contemplates the provision of mixed ligand monomeric Cp complexes of ruthenium (II) in which the non-Cp ligand can be a nitrogen-based amidinate, guanidinate, beta-diketoiminate, beta-diketiminate, or related ligand.

Such mixed ligand Cp ruthenium precursors can be readily synthesized by suitable techniques, such as the reaction of compounds such as [Cp*RuCl]$_4$ and [Cp*RuOCH$_3$]$_2$ with lithium salts of corresponding amidinates, guanidinates, beta-diketiminates, or related ligands.

Various substituted cyclopentadiene ligands can also be used in such synthesis, to yield the desired monomeric precursor via a salt elimination pathway. The specific nitrogen ligands selected for such synthesis are chosen to provide enough steric bulk to yield monomeric precursor species with sufficient volatility for transport and the deposition of the ruthenium metal.

The cyclopentadiene ligands may be appropriately substituted to achieve such suitable volatile monomeric character. By way of specific example, in the case of acetylacetonate ligands, relatively large substituents as tert-butyl may be employed to prevent dimerization.

In one aspect, the invention relates to mixed ligand monomeric Cp complexes of ruthenium (Ru) selected from among:
(1) ruthenium beta-diketiminate compounds of the formula

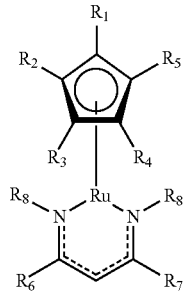

wherein each of $R_1$, $R_2$, $R_3$, $R_4$, $R_5$, $R_6$, $R_7$, and $R_8$ can be the same as or different from the others, and is independently selected from hydrogen, $C_1$-$C_6$ alkyl, $C_6$-$C_{10}$ aryl, $C_1$-$C_6$ alkylamine, silyl, and substituted silyl wherein the silyl substituents can be any suitable organo substituents, e.g., $C_1$-$C_6$ alkyl, such as trimethylsilyl;
(2) ruthenium beta-diketoiminate compounds of the formula

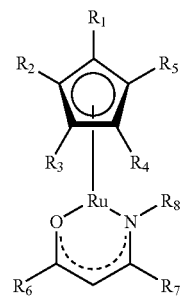

wherein each of $R_1$, $R_2$, $R_3$, $R_4$, $R_5$, $R_6$, $R_7$, and $R_8$ can be the same as or different from the others, and is independently selected from hydrogen, $C_1$-$C_6$ alkyl, $C_6$-$C_{10}$ aryl, $C_1$-$C_6$ alkylamine, silyl, and substituted silyl wherein the silyl substituents can be any suitable organo substituents, e.g., $C_1$-$C_6$ alkyl, such as trimethylsilyl;
(3) ruthenium acetylacetonate compounds of the formula

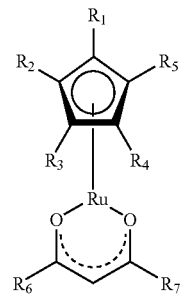

wherein each of $R_1$, $R_2$, $R_3$, $R_4$, $R_5$, $R_6$, and $R_7$ can be the same as or different from the others, and is independently selected from hydrogen, $C_1$-$C_6$ alkyl, $C_6$-$C_{10}$ aryl, $C_1$-$C_6$ alkylamine, silyl, and substituted silyl wherein the silyl substituents can be any suitable organo substituents, e.g., $C_1$-$C_6$ alkyl, such as trimethylsilyl;

(4) ruthenium amidinate compounds of the formula:

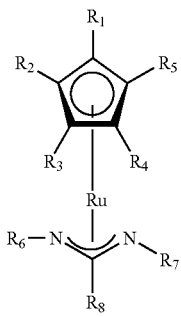

wherein each of $R_1$, $R_2$, $R_3$, $R_4$, $R_5$, $R_6$, $R_7$, and $R_8$ can be the same as or different from the others, and is independently selected from hydrogen, $C_1$-$C_5$ alkyl, $C_6$-$C_{10}$ aryl, $C_3$-$C_9$ cycloalkyl, silyl, and substituted silyl wherein the silyl substituents can be any suitable organo substituents, e.g., $C_1$-$C_6$ alkyl, such as trimethylsilyl;
(5) ruthenium guanidinate compounds of the formula:

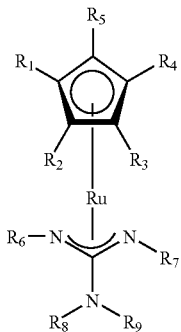

wherein each of $R_1$, $R_2$, $R_3$, $R_4$, $R_5$, $R_6$, $R_7$, $R_8$ and $R_9$ can be the same as or different from the others, and is independently selected from hydrogen, $C_1$-$C_5$ alkyl, $C_6$-$C_{10}$ aryl, $C_3$-$C_9$ cycloalkyl, silyl, and substituted silyl wherein the silyl substituents can be any suitable organo substituents, e.g., $C_1$-$C_6$ alkyl, such as trimethylsilyl;
6) ruthenium isoureate compounds and formula

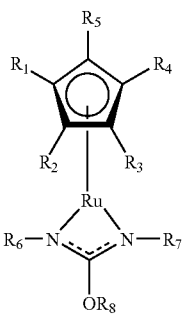

wherein each of $R_1$, $R_2$, $R_3$, $R_4$, $R_5$, $R_6$, $R_7$ and $R_8$ can be the same as or different from the others, and is independently selected from hydrogen, $C_1$-$C_5$ alkyl, $C_6$-$C_{10}$ aryl, $C_3$-$C_9$ cycloalkyl, silyl, and substituted silyl wherein the silyl substituents can be any suitable organo substituents, e.g., $C_1$-$C_6$ alkyl, such as trimethylsilyl.

The synthesis of the ruthenium beta-diketiminates can be carried out in a specific implementation by a salt elimination reaction as set out below.

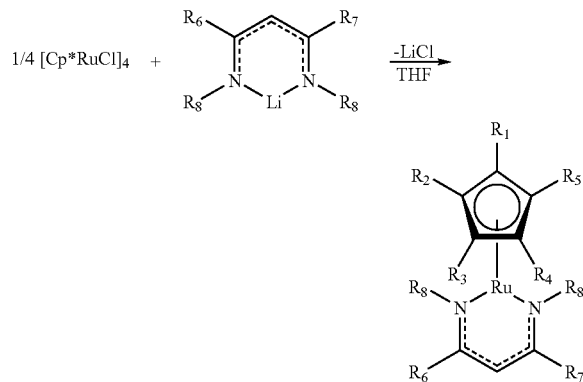

wherein each of $R_1$, $R_2$, $R_3$, $R_4$, $R_5$, $R_6$, $R_7$, and $R_8$ can be the same as or different from the others, and is independently selected from hydrogen, $C_1$-$C_6$ alkyl, $C_6$-$C_{10}$ aryl, $C_1$-$C_6$ alkylamine, silyl, and substituted silyl wherein the silyl substituents can be any suitable organo substituents, e.g., $C_1$-$C_6$ alkyl, such as trimethylsilyl.

As an alternative, the ruthenium beta-diketiminates can be synthesized by an amine elimination synthesis route as set out below:

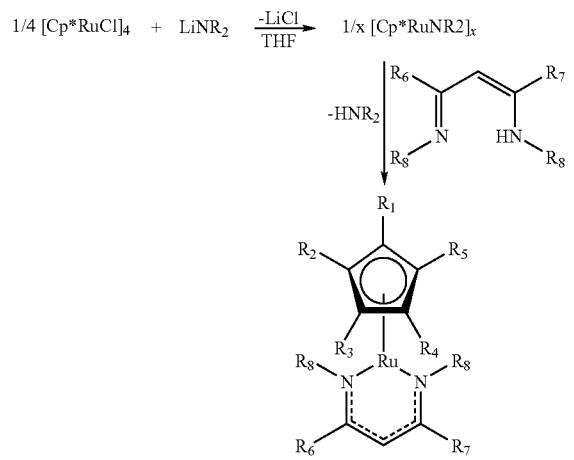

wherein each of $R_1$, $R_2$, $R_3$, $R_4$, $R_5$, $R_6$, $R_7$, and $R_8$ can be the same as or different from the others, and is independently selected from hydrogen, $C_1$-$C_6$ alkyl, $C_6$-$C_{10}$ aryl, $C_1$-$C_6$ alkylamine, silyl, and substituted silyl wherein the silyl substituents can be any suitable organo substituents, e.g., $C_1$-$C_6$ alkyl, such as trimethylsilyl.

The ruthenium-diketoiminates of the invention can be made by a synthesis including the following reaction:

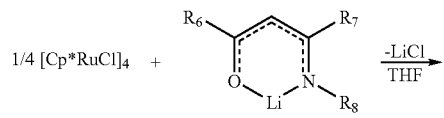

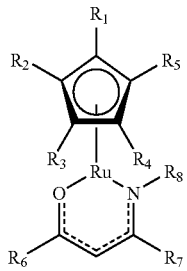

wherein each of $R_1$, $R_2$, $R_3$, $R_4$, $R_5$, $R_6$, $R_7$, and $R_8$ can be the same as or different from the others, and is independently selected from hydrogen, $C_1$-$C_6$ alkyl, $C_6$-$C_{10}$ aryl, $C_1$-$C_6$ alkylamine, silyl, and substituted silyl wherein the silyl substituents can be any suitable organo substituents, e.g., $C_1$-$C_6$ alkyl, such as trimethylsilyl.

Ruthenium-acetylacetonates can be synthesized by the following synthesis reaction:

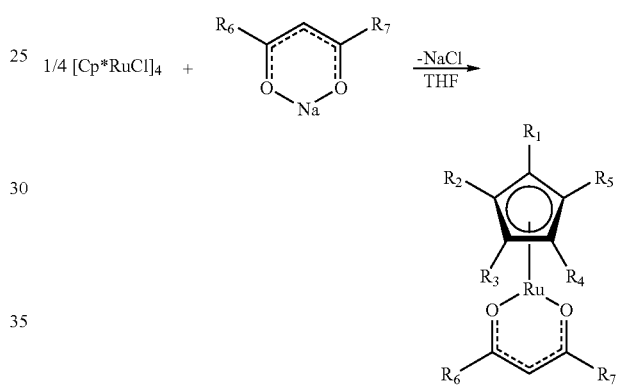

wherein each of $R_1$, $R_2$, $R_3$, $R_4$, $R_5$, $R_6$, and $R_7$ can be the same as or different from the others, and is independently selected from hydrogen, $C_1$-$C_6$ alkyl, $C_6$-$C_{10}$ aryl, $C_1$-$C_6$ alkylamine, silyl, and substituted silyl wherein the silyl substituents can be any suitable organo substituents, e.g., $C_1$-$C_6$ alkyl, such as trimethylsilyl.

The mixed ligand Cp ruthenium compounds of the invention can be supplied in any suitable form for volatilization to produce the precursor vapor for deposition contacting with the substrate, e.g., in a liquid form that is vaporized or as a solid that is dissolved or suspended in a solvent medium for flash vaporization, as a sublimable solid, or as a solid having sufficient vapor pressure to render it suitable for vapor delivery to the deposition chamber, or in any other suitable form.

When solvents are employed for delivery of the precursors of the invention, any suitable solvent media can be employed in which the precursor can be dissolved or dispersed for delivery. By way of example, the solvent medium may be a single-component solvent or a multicomponent solvent mixture, including solvent species such as $C_3$-$C_{12}$ alkanes, $C_2$-$C_{12}$ ethers, $C_6$-$C_{12}$ aromatics, $C_7$-$C_{16}$ arylalkanes, $C_{10}$-$C_{25}$ arylcyloalkanes, and further alkyl-substituted form of aromatic, arylalkane and arylcyloalkane species, wherein the further alkyl substituents in the case of multiple alkyl substituents may be the same as or different from one another and wherein each is independently selected from $C_1$-$C_8$ alkyl. Illustrative solvents include amines, ethers, aromatic solvents, glymes, tetraglymes, alkanes, alkyl-substituted benzene compounds, benzocyclohexane (tetralin), alkyl-substituted benzocyclohexane and ethers, with tetrahydrofuran, xylene, 1,4-tertbutyltoluene, 1,3-diisopropylbenzene, tetralin, dimethyltetralin, octane and decane being potentially useful solvent species in specific applications.

In instances where liquid delivery is employed in deposition processes of the invention to form deposited metal films, it may be preferable to utilize high boiling point solvents in order to avoid metal precursor deposits in the delivery system, such as in flow circuitry, and in vaporizers that are utilized to volatilize the metal precursor to form a corresponding precursor vapor, where the system is otherwise susceptible to solids deposition and clogging.

Accordingly, in various embodiments of the invention, it may be desirable to utilize high boiling aromatic solvents, e.g., aromatic solvents having a boiling point at 1 atmosphere pressure in a range of from about 140° C. to about 250° C. For example, in liquid delivery ruthenium precursor applications for atomic layer deposition processes, suitable solvents may include xylene, 1,4-tertbutyltoluene, 1,3-diisopropylbenzene, tetralin, dimethyltetralin and other alkyl-substituted aromatic solvents. The solvent medium may also comprise a stabilizing solvent, e.g., a Lewis-base ligand.

In general, the precursor compositions of the invention may alternatively comprise, consist, or consist essentially of any of the components and functional moieties disclosed herein, in specific embodiments of the invention.

The invention in another aspect relates to mixed ligand Cp compounds of the foregoing formulae (1)-(5), wherein the metal center instead of ruthenium is strontium, calcium, or barium. Strontium, calcium, and barium compounds of such type have utility as ALD and CVD precursors for depositing corresponding metal films.

The invention in another aspect relates to precursors useful for conformal deposition, via ALD and CVD techniques, of ruthenium-containing films, e.g., a strontium ruthenium oxide (SRO) thin film, in which the precursors are selected from among:

A) $Ru(Cp)_2$ and $Sr(Cp)_2$, wherein Cp is cyclopentadienyl of the formula

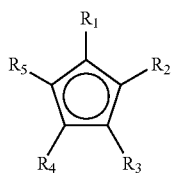

wherein each of $R_1$, $R_2$, $R_3$, $R_4$ and $R_5$ to R5 can be the same as or different from the others, and each is independently selected from among hydrogen, $C_1$ to $C_6$ alkyl, $C_6$ to $C_{10}$ aryl, $C_1$ to $C_6$ alkoxy, $C_1$ to $C_6$ alkylsilyl, and pendant ligands with additional functional group(s) that can provide further coordination to the metal center, such as $-(CH_2)_n-NR_2$, and $-(CH_2)_n-OR$, wherein n is an integer having a value in a range of from 1 to 4, and each R is independently selected from among hydrogen, $C_1$ to $C_6$ alkyl, $C_6$ to $C_{10}$ aryl, $C_1$ to $C_6$ alkoxy, and $C_1$ to $C_6$ alkylsilyl, as well as pendent ligands previously described;

B) $Ru(beta\text{-}diketonate)_x\text{-}L_y$ and $Sr(beta\text{-}diketonate)_2\text{-}L_z$ wherein the beta-diketonate moiety has the formula

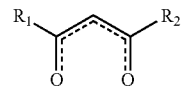

wherein:
x has a value of 2 or 3, y is an integer having a value of from 0 to 2, and z is an integer having a value of from 0 to 4;
$R_1$ and $R_2$ can be the same as or different from one another, and each is independently selected from among $C_1$ to $C_6$ alkyl, $C_6$ to $C_{10}$ aryl, $C_1$ to $C_6$ alkoxy, $C_1$ to $C_6$ alkylsilyl, and pendant ligands with additional functional group(s) that can provide further coordination to the metal center, such as $-(CH_2)_n-NR_2$, and $-(CH_2)_n-OR$, wherein n is an integer having a value in a range of from 1 to 4; and
L is selected from among neutral Lewis bases, such as amines (e.g., PMDETA), $C_2$ to $C_{12}$ ethers (e.g., THF), tetraglymes, $C_2$ to $C_{12}$ alkenes (e.g., cyclooctane-1,5-diene (COD), and $C_2$ to $C_{12}$ alkynes;

C) $Ru(beta\text{-}diketoiminate)_x\text{-}L_y$ and $Sr(beta\text{-}diketoiminate)_2\text{-}L_z$ wherein beta-diketoiminate has the formula

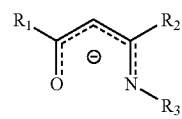

wherein:
x has a value of 2 or 3, y is an integer having a value of from 0 to 2, and z is an integer having a value of from 0 to 4;
each of $R_1$, $R_2$ and $R_3$ can be the same as or different from one another, and each is independently selected from among $C_1$ to $C_6$ alkyl, $C_6$ to $C_{10}$ aryl, $C_1$ to $C_6$ alkoxy, $C_1$ to $C_6$ alkylsilyl, and pendant ligands with additional functional group(s) that can provide further coordination to the metal center, such as $-(CH_2)_n-NR_2$, and $-(CH_2)_n-OR$, wherein n is an integer having a value in a range of from 1 to 4; and
L is selected from among neutral Lewis bases, such as amines (e.g., PMDETA), $C_2$ to $C_{12}$ ethers (e.g., THF), tetraglymes, $C_2$ to $C_{12}$ alkenes (e.g., cyclooctane-1,5-diene (COD), and $C_2$ to $C_{12}$ alkynes; and D) $Ru(beta\text{-}diketiminate)_x\text{-}L_y$ and $Sr(beta\text{-}diketiminate)_2\text{-}L_z$, wherein beta-diketiminate has the formula

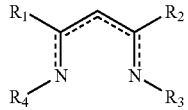

wherein:
x has a value of 2 or 3, y is an integer having a value of from 0 to 2, and z is an integer having a value of from 0 to 4;
$R_1$, $R_2$, $R_3$ and $R_4$ can be the same as or different from one another, and each is independently selected from among $C_1$ to $C_6$ alkyl, $C_6$ to $C_{10}$ aryl, $C_1$ to $C_6$ alkoxy, $C_1$ to $C_6$ alkylsilyl, and pendant ligands with additional functional group(s) that can provide further coordination to the metal center, such as —(CH$_2$)$_n$—NR$_2$, and —(CH$_2$)$_n$—OR, wherein n is an integer having a value in a range of from 1 to 4; and L is selected from among neutral Lewis bases, such as amines (e.g., PMDETA), C$_2$ to C$_{12}$ ethers (e.g., THF), tetraglymes, C$_2$ to C$_{12}$ alkenes (e.g., cyclooctane-1,5-diene (COD), and C$_2$ to C$_{12}$ alkynes.

In specific embodiments of the invention, the precursors A)-D) may be constituted as a selection group in which Sr(CpMe$_5$)$_2$, EtCp$_2$Ru, Sr(thd)$_2$-PMDETA are excluded by appropriate restriction of selection criteria.

Precursor species within each of the above-described precursor classes A)-D) are chemically compatible, and can be utilized in combinations, in which two or more of such precursors of a given class are mixed with one another, e.g., in a solution as a precursor cocktail composition for liquid delivery, as a simple and efficient approach to the deposition of strontium and/or ruthenium films.

Alternatively, the precursor species may be individually dissolved in solvent(s) and delivered into vaporizers for volatilization of the precursor solution to form a precursor vapor that then is transported to the deposition chamber of the deposition system to deposit strontium and/or ruthenium on a wafer or other microelectronic device substrate.

Thus, the precursors may be supplied in liquid delivery systems as individual precursors or mixtures of precursors, in solvent media that may be comprised of a single component solvent, or alternatively may be constituted by a solvent mixture, as appropriate in a given application. The solvents that may be employed for such purpose can be of any suitable type in which the specific precursor(s) can be dissolved or suspended, and subsequently volatilized to form the precursor vapor for contacting with the substrate on which the metal is to be deposited. Illustrative of solvents that may usefully be employed in specific applications are hydrocarbon solvents, such as amine solvents, neutral amines such as DMAPA, octane or other aliphatic solvents, aromatic solvents such as toluene, ethers such as tetrahydrofuran (THF), and tetraglymes.

As a still further alternative, the precursors A)-D) can be delivered by solid delivery techniques, in which the solid is volatilized to form the precursor vapor that then is transported to the deposition chamber, and with the solid precursor in the first instance being supplied in a packaged form for use, e.g., in a ProE-Vap package (ATMI, Inc., Danbury, Conn., USA).

The precursors A)-D) of the present invention are usefully employed for forming SRO thin films of high conformality and uniformity characteristics, by ALD and CVD processes. The process conditions for the deposition process in a specific application may be readily determined empirically by variation of specific conditions (temperature, pressure, flow rate, concentration, etc.) and characterization of the resulting film deposit.

In the formation of SRO films, any suitable co-reactant or carrier species may be employed, e.g., oxidants, producing agents, inert gases, etc. In a specific embodiment in which an oxidant is used, the oxidant employed in the deposition may be of any suitable type, e.g., nitrous oxide, oxygen, ozone, water, alcohols, or other suitable oxidant. The co-reactants may be supplied simultaneously, e.g., with the precursors entering the deposition chamber concurrently, in a chemical vapor deposition mode, or separately from the precursors, in an atomic layer deposition or digital CVD mode. The precursors can be employed in an ALD mode, in which a purge pulse separates them from the co-reactants, and matched or unmatched precursors may be used. In a pulsed method, the Sr and Ru can be introduced in separate pulses or be delivered in the same pulse.

The cyclopentadienyl precursors of the invention are particularly useful in atomic layer deposition (ALD) processes. In an illustrative ALD process for forming an SRO layer, a substrate having suitable pre-existing structural layers thereon is subjected to contact with ruthenium precursor under deposition conditions resulting in the surface, e.g., of another metal, being functionalized with ruthenium moieties. The thus-functionalized structure then is subjected to contact with oxidant [O] such as oxygen, ozone, etc., or water. A wide variety of oxidants can be used for such purpose. The surface then reacts with the oxidant to form a hydroxylated surface.

The hydroxylated surface of the device structure next is contacted with the strontium reagent to yield the strontiated (strontium-functionalized) surface. The strontiated surface then is contacted with oxidant or water to form the hydroxylated surface, and the hydroxylated surface thereafter is processed by contact with the ruthenium precursor, with repetition of the above-described steps, has carried out any suitable number of times to build up a layer of strontium ruthenium oxide, SrRuO$_3$.

In this repetitive manner, a film of strontium ruthenium oxide is built up over in the device structure, with the deposition process being conducted through multiple steps of ruthenium functionalization, hydroxylation, strontiation and hydroxylation, to build up the strontium ruthenium oxide film to a desired thickness.

Analogous processes can be carried out utilizing alternating layers of other metal species, to form other metal film compositions containing ruthenium and strontium, calcium or barium.

In one embodiment of the above-described process, the oxidant is selected from among oxygen, ozone and oxygen plasma. The use of such oxidant may eliminate the need for a final annealing step, such as rapid thermal annealing.

In general, the thicknesses of the ruthenium, strontium and SRO layers in the practice of the present invention can be of any suitable value. In a specific embodiment of the invention, the thickness of the SRO layer can be in a range of from 5 nm to 500 nm or more. As used herein, the term "thin-film" refers to a layer of material having a thickness less than 1 µm.

Set out in Table 1 below are x-ray diffraction/x-ray fluorescence data that were generated for a ruthenium layer that was deposited from Ru(EtCp)$_2$ under varied conditions of temperature and oxygen concentration in an 8 Torr deposition ambient environment, both under conditions where either forming gas (4% H$_2$) or inert gas (Inert) were used to make-up the non-oxygen part of the deposition ambient.

TABLE 1

| | 2% O$_2$ | | 15% O$_2$ | | 80% O$_2$ | |
|---|---|---|---|---|---|---|
| | H$_2$ | Inert | H$_2$ | Inert | H$_2$ | Inert |
| 345° C. | 45/M | 53/M | 88/M | 116/M | 91/Ox | 99/Ox |
| | 423/∞ | 222/∞ | 448/∞ | 295/1000 | 317/350 | 439/402 |
| | 145/700 | 139/635 | 167/948 | 113/689 | 90/784 | 86/639 |
| 300° C. | 4 | | 0 | | | 87, 87/Ox |
| | 0 | | 58 | | | 394, 378/ |
| | | | | | | 610, 490 |
| | | | | | | 39/313 |
| 260° C. | 4 | | 0 | | | 30/Ox |
| | 0 | | 60 | | | 141/660 |
| | | | | | | 21/170 |

FIG. 1 is a corresponding measure of the ruthenium deposition from Ru(EtCp)$_2$ under a broader range of conditions determined by such x-ray diffraction (XRD) and x-ray fluorescence (XRF) techniques, and based on the data in Table 1, in which the respective axes represent oxygen concentration (O$_2$), pressure (P), and temperature (T). Taken together, the data in Table 1 and FIG. 1 show that Ru does not deposit from Ru(EtCp)$_2$ under inert or forming gas conditions. This is in contrast to the fast deposition reported in the literature for metallic surfaces.

The invention in another aspect relates to formation of Group II metal ruthenate films, wherein the Group II metal includes one or more of strontium, calcium and barium, and the Group II ruthenate film is formed by deposition using a precursor composition including a ruthenium precursor and Group II precursor(s). The Group II precursor(s) include at least one of a strontium precursor, a calcium precursor and a barium precursor.

In a specific embodiment of the invention, such ruthenium precursor and the Group II precursor(s) have compatible ligands, the term "compatible" in such context referring to the fact that there is at least one common ligand between the ruthenium precursor and the Group II precursor(s).

By way of specific example, the ruthenium precursor in one such compatible composition may have a cyclopentadienyl ligand, and each of the one or more Group II precursors used with the ruthenium reagent also has a cyclopentadienyl ligand. In another specific example, the ruthenium precursor as a beta-diketonate ligand, and each of the one or more Group II precursors used with the ruthenium reagent likewise has a beta-diketonate ligand.

Beta-diketonate ligands that may be utilized in such compatible groupings may be of any suitable type, including for example, 2,2,6,6-tetramethyl-3,5-heptanedionate; 1,1,1,5,5, 5-hexafluoro-2,4-pentanedionate; and 1,1,1,2,2,3,3-heptafluoro-7,7-dimethyl-4,6-octanedionate.

Additional compatible groupings include those in which each of the ruthenium precursor and the associated one or more Group II precursors includes di-cyclopentadienyl moieties, and those in which each of the ruthenium precursor and the associated one or more Group II precursors includes a 2,2,6,6-tetramethyl-3,5-heptanedionate ligand, also referred to as "thd," with the ruthenium precursor being of the formula Ru(thd)$_3$ and the Group II precursor being a strontium precursor of the formula Sr(thd)$_2$(pmdeta), in which pmdeta represents pentamethyldiethylenetriamine.

The invention therefore contemplates the use for deposition of a ruthenate film of a ruthenium precursor and one or more corresponding strontium, calcium and/or barium precursors containing a common ligand in each of the precursors. In one specific embodiment, the invention contemplates a precursor vapor comprising vapor of constituent precursors including a ruthenium precursor and at least one strontium/calcium/barium precursor, in which each of such precursor species has a common ligand.

The invention also contemplates the provision in ALD or digital CVD applications of respective ruthenium and Group II precursor(s) lacking any common ligand, in which the ruthenium precursor exposure to the substrate is separated from the Group II precursor exposure to the substrate by a purge pulse therebetween. An illustrative example of such "disparate ligand" precursor groupings is the contacting of the substrate with a Group II strontium, calcium or barium precursor having a dicyclopentadienyl ligand, with such contacting separated by a purge pulse from the contacting of the substrate with a ruthenium precursor of the formula Ru(thd)$_3$.

Figure 2:
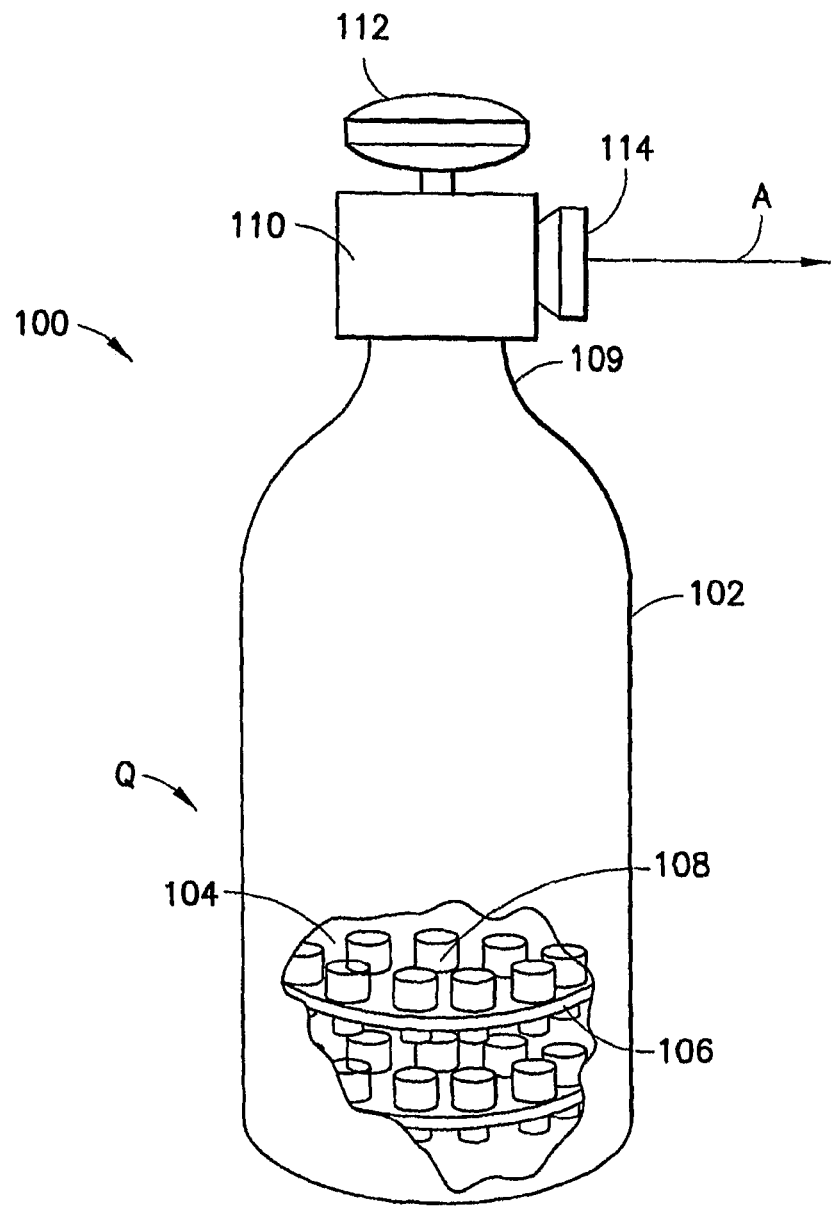
FIG. 2 is a schematic representation of a material storage and dispensing package containing a ruthenium precursor, according to one embodiment of the present invention.

FIG. 2 is a schematic representation of a material storage and dispensing package 100 containing a ruthenium precursor, according to one embodiment of the present invention.

The material storage and dispensing package 100 includes a vessel 102 that may for example be of generally cylindrical shape as illustrated, defining an interior volume 104 therein. In this specific embodiment, the ruthenium precursor is a solid at ambient temperature conditions, and such precursor may be supported on surfaces of the trays 106 disposed in the interior volume 104 of the vessel, with the trays having flow passage conduits 108 associated therewith, for flow of vapor upwardly in the vessel to the valve head assembly, for dispensing in use of the vessel.

The solid precursor can be coated on interior surfaces in the interior volume of the vessel, e.g., on the surfaces of the trays 106 and conduits 108. Such coating may be effected by introduction of the precursor into the vessel in a vapor form from which the solid precursor is condensed in a film on the surfaces in the vessel. Alternatively, the precursor solid may be dissolved or suspended in a solvent medium and deposited on surfaces in the interior volume of the vessel by solvent evaporation. In yet another method the precursor may be melted and poured onto the surfaces in the interior volume of the vessel. For such purpose, the vessel may contain substrate articles or elements that provide additional surface area in the vessel for support of the precursor film thereon.

As a still further alternative, the solid precursor may be provided in granular or finely divided form, which is poured into the vessel to be retained on the top supporting surfaces of the respective trays 106 therein.

The vessel 102 has a neck portion 109 to which is joined the valve head assembly 110. The valve head assembly is equipped with a hand wheel 112 in the embodiment shown. The valve head assembly 110 includes a dispensing port 114, which may be configured for coupling to a fitting or connection element to join flow circuitry to the vessel. Such flow circuitry is schematically represented by arrow A in FIG. 4, and the flow circuitry may be coupled to a downstream ALD or chemical vapor deposition chamber (not shown in FIG. 4).

In use, the vessel 102 is heated, such input of heat being schematically shown by the reference arrow Q, so that solid precursor in the vessel is at least partially volatilized to provide precursor vapor. The precursor vapor is discharged from the vessel through the valve passages in the valve head assembly 110 when the hand wheel 112 is translated to an open valve position, whereupon vapor deriving from the precursor is dispensed into the flow circuitry schematically indicated by arrow A.

In lieu of solid delivery of the precursor, the precursor may be provided in a solvent medium, forming a solution or suspension. Such precursor-containing solvent composition then may be delivered by liquid delivery and flash vaporized to produce a precursor vapor. The precursor vapor is contacted with a substrate under deposition conditions, to deposit the metal on the substrate as a film thereon.

In one embodiment, the precursor is dissolved in an ionic liquid medium, from which precursor vapor is withdrawn from the ionic liquid solution under dispensing conditions.

As a still further alternative, the precursor may be stored in an adsorbed state on a suitable solid-phase physical adsorbent storage medium in the interior volume of the vessel. In use, the precursor vapor is dispensed from the vessel under dispensing conditions involving desorption of the adsorbed precursor from the solid-phase physical adsorbent storage medium.

Supply vessels for precursor delivery may be of widely varying type, and may employ vessels such as those commercially available from ATMI, Inc. (Danbury, Conn.) under the trademarks SDS, SAGE, VAC, VACSorb, and ProE-Vap, as may be appropriate in a given storage and dispensing application for a particular precursor of the invention.

The precursors of the invention thus may be employed to form precursor vapor for contacting with a substrate to deposit a thin film of ruthenium thereon, in connection with concurrent or sequential deposition of strontium from a suitable strontium source reagent, to produce ruthenium films, strontium films, or ruthenium/strontium films. Other Group II source reagents can be employed to form CaRuO or BaRuO films.

In a preferred aspect, the invention utilizes the ruthenium precursors to conduct atomic layer deposition in connection with the use of a suitable strontium source reagent, yielding ALD films of superior conformality that are uniformly coated on the substrate with high step coverage even on high aspect ratio structures.

Accordingly, the ruthenium precursors of the present invention enable a wide variety of microelectronic devices, e.g., semiconductor products, flat panel displays, etc., to be fabricated with ruthenium-containing films of superior quality.

While the invention has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A composition, comprising a compound or complex comprising a ruthenium compound containing at least one cyclopentadienyl ligand, and at least one further ligand selected from among guanidinate and beta-diketiminate ligands.

2. A composition comprising a compound or complex comprising a mixed ligand monomeric Cp complex of ruthenium, calcium strontium or barium, selected from among:
ruthenium beta-diketiminate compounds of the formula

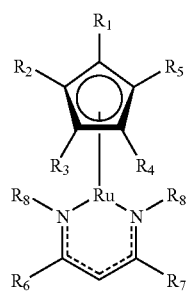

wherein each of $R_1$, $R_2$, $R_3$, $R_4$ and $R_5$ can be the same as or different from the others, and each is independently selected from among hydrogen, $C_1$-$C_{12}$ alkyl, $C_1$-$C_{12}$ alkylamino, $C_3$-$C_8$ cycloalkyl, $C_6$-$C_{12}$ aryl, $C_5$-$C_{12}$ heteroaryl, $C_1$-$C_{12}$ alkoxy, $C_3$-$C_6$ alkylsilyl, $C_2$-$C_{12}$ alkenyl, $R^1R^2NNR^3$, wherein $R^1$, $R^2$ and $R^3$ may be the same as or different from one another and each is independently selected from hydrogen and $C_1$-$C_6$ alkyl, and pendant ligands including functional group(s) providing further coordination to the ruthenium central atom, and selected from among aminoalkyl, alkoxyalkyl, aryloxyalkyl, imidoalkyl, and acetylalkyl, and wherein each of $R_6$, $R_7$, and $R_8$ can be the same as or different from the others, and is independently selected from hydrogen, $C_1$-$C_6$ alkyl, $C_6$-$C_{10}$ aryl, $C_1$-$C_6$ alkylamine, silyl and substituted silyl.

3. A composition comprising a compound or complex comprising a mixed ligand monomeric Cp complex of ruthenium, calcium, strontium or barium, selected from among:
ruthenium beta-diketoiminate compounds of the formula

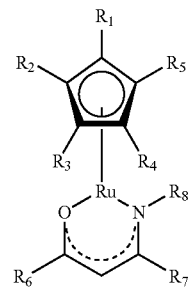

wherein each of $R_1$, $R_2$, $R_3$, $R_4$ and $R_5$ can be the same as or different from the others, and each is independently selected from among hydrogen, $C_1$-$C_{12}$ alkyl, $C_1$-$C_{12}$ alkylamino, $C_3$-$C_8$ cycloalkyl, $C_6$-$C_{12}$ aryl, $C_5$-$C_{12}$ heteroaryl, $C_1$-$C_{12}$ alkoxy, $C_3$-$C_6$ alkylsilyl, $C_2$-$C_{12}$ alkenyl, $R^1R^2NNR^3$, wherein $R^1$, $R^2$ and $R^3$ may be the same as or different from one another and each is independently selected from hydrogen and $C_1$-$C_6$ alkyl, and pendant ligands including functional group(s) providing further coordination to the ruthenium central atom, and selected from among aminoalkyl, alkoxyalkyl, aryloxyalkyl, imidoalkyl, and acetylalkyl, and wherein each of $R_6$, $R_7$, and $R_8$ can be the same as or different from the others, and is independently selected from $C_1$-$C_6$ alkyl, $C_6$-$C_{10}$ aryl, $C_1$-$C_6$ alkylamine, silyl and substituted silyl.

4. A composition comprising a compound or complex comprising a mixed ligand monomeric Cp complex of ruthenium, calcium, strontium or barium, selected from among:
ruthenium guanidinate compounds of the formula:

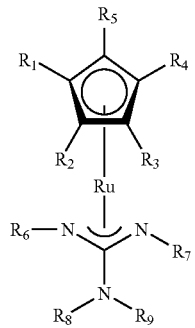

wherein each of $R_1$, $R_2$, $R_3$, $R_4$ and $R_5$ can be the same as or different from the others, and each is independently selected from among hydrogen, $C_1$-$C_{12}$ alkyl, $C_1$-$C_{12}$ alkylamino, $C_3$-$C_8$ cycloalkyl, $C_6$-$C_{12}$ aryl, $C_5$-$C_{12}$ heteroaryl, $C_1$-$C_{12}$ alkoxy, $C_3$-$C_6$ alkylsilyl, $C_2$-$C_{12}$ alkenyl, $R^1R^2NNR^3$, wherein $R^1$, $R^2$ and $R^3$ may be the same as or different from one another and each is independently selected from hydrogen and $C_1$-$C_6$ alkyl, and pendant ligands including functional group(s) providing further coordination to the ruthenium central atom, and selected from among aminoalkyl, alkoxyalkyl, aryloxyalkyl, imidoalkyl, and acetylalkyl, and wherein each of $R_6$, $R_7$, $R_8$ and $R_9$ can be the same as or different from the others, and is independently selected from hydrogen, $C_1$-$C_5$ alkyl, $C_6$-$C_{10}$ aryl, $C_3$-$C_9$ cycloalkyl, silyl and substituted silyl.

* * * * *